US011002815B2

(12) United States Patent
Wang

(10) Patent No.: US 11,002,815 B2
(45) Date of Patent: May 11, 2021

(54) SYSTEM AND METHOD FOR REDUCING ARTIFACTS IN ECHO PLANAR MAGNETIC RESONANCE IMAGING

(71) Applicant: University of Cincinnati, Cincinnati, OH (US)

(72) Inventor: Jinghua Wang, Mason, OH (US)

(73) Assignee: UNIVERSITY OF CINCINNATI, Cincinnati, OH (US)

( * ) Notice: Subject to any disclaimer, the term of this patent is extended or adjusted under 35 U.S.C. 154(b) by 0 days.

(21) Appl. No.: 16/825,479

(22) Filed: Mar. 20, 2020

(65) Prior Publication Data
US 2020/0300947 A1  Sep. 24, 2020

Related U.S. Application Data

(60) Provisional application No. 62/821,635, filed on Mar. 21, 2019.

(51) Int. Cl.
*G01R 33/48* (2006.01)
*G01R 33/561* (2006.01)
(Continued)

(52) U.S. Cl.
CPC .......... *G01R 33/4818* (2013.01); *A61B 5/055* (2013.01); *G01R 33/5608* (2013.01);
(Continued)

(58) Field of Classification Search
CPC ............ G01R 33/4818; G01R 33/5608; G01R 33/5611; G01R 33/5616; G01R 33/56554; A61B 5/055
See application file for complete search history.

(56) References Cited

U.S. PATENT DOCUMENTS 6,043,651 A   3/2000 Heid
7,772,847 B2  8/2010 Zur
(Continued)

FOREIGN PATENT DOCUMENTS

WO   2016180983 A1   11/2016

OTHER PUBLICATIONS

Akçakaya, et al., "Scan-specific Robust Artificial-neural-networks for k-space Interpolation (RAKI) Reconstruction: Database-free Deep Learning for Fast Imaging," in Magnetic Resonance in Medicine, Jan. 2019, 81(1): 439-453. doi:10.1002/mrm.27420.

*Primary Examiner* — Gregory H Curran
(74) *Attorney, Agent, or Firm* — Dinsmore & Shohl LLP

(57) ABSTRACT

A method for reducing N/2 ghost or Nyquist ghost in magnetic resonance (MR) images is provided The method includes acquiring k-space dataset for an object using an echo planar imaging (EPI) sequence, dividing the k-space dataset into first partial k-space subset data related to positive echoes and second partial k-space subset data related to negative echoes, obtaining third partial k-space subset data that is N/2 or Nyquist ghost-free subset data, respectively registering the first partial k-space subset data and the second partial k-space subset data to a first portion of the third partial k-space subset data corresponding to positive echoes and a second portion of the third partial k-space subset data corresponding to negative echoes, combining the registered first partial k-space subset data and the registered second partial k-space subset data to form full k-space dataset, and reconstructing an image for the object based on the full k-space dataset.

20 Claims, 10 Drawing Sheets

(51) Int. Cl.
  *A61B 5/055* (2006.01)
  *G01R 33/565* (2006.01)
  *G01R 33/56* (2006.01)
(52) U.S. Cl.
  CPC ...... *G01R 33/5611* (2013.01); *G01R 33/5616* (2013.01); *G01R 33/56554* (2013.01)

(56) References Cited

U.S. PATENT DOCUMENTS

| | | |
|---|---|---|
| 8,023,705 B2 | 9/2011 | Weng et al. |
| 8,497,681 B2 | 7/2013 | Feiweier |
| 9,612,307 B2 | 4/2017 | Zhou |
| 9,880,247 B2 | 1/2018 | Muftuler et al. |
| 9,886,745 B2 | 2/2018 | Chen et al. |
| 9,933,505 B2 | 4/2018 | Pipe |
| 9,989,606 B2 | 6/2018 | Foxall |
| 2002/0156364 A1* | 10/2002 | Madore .............. G01R 33/5611 600/410 |
| 2012/0008842 A1* | 1/2012 | Hinks .............. G01R 33/56554 382/131 |
| 2015/0355303 A1* | 12/2015 | Kuhara .............. G01R 33/5611 324/322 |
| 2017/0089999 A1 | 3/2017 | Zeller et al. |
| 2017/0108571 A1 | 4/2017 | Jurrissen et al. |
| 2017/0307717 A1 | 10/2017 | Geraghty et al. |
| 2018/0238986 A1 | 8/2018 | De Weerdt et al. |
| 2018/0335495 A1 | 11/2018 | Stainsby et al. |

\* cited by examiner

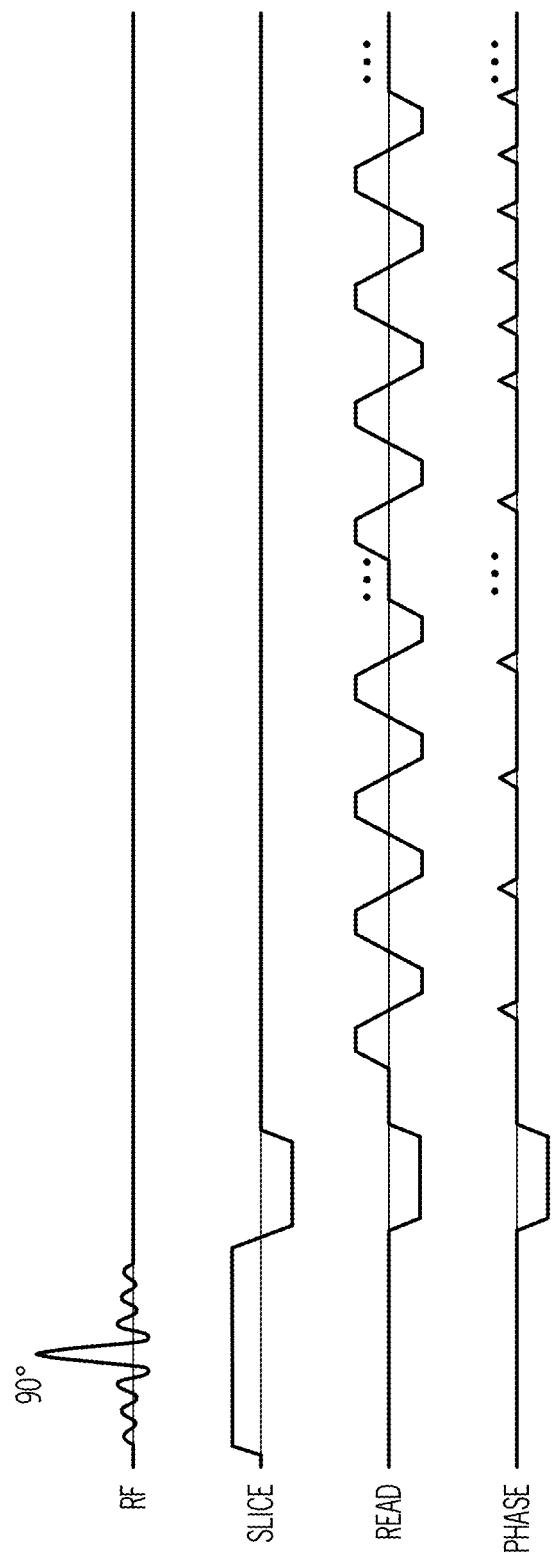

SYSTEM AND METHOD FOR REDUCING ARTIFACTS IN ECHO PLANAR MAGNETIC RESONANCE IMAGING

CROSS-REFERENCE TO RELATED APPLICATION

This application claims benefit of U.S. Provisional Application No. 62/821,635 filed on Mar. 21, 2019, the entire contents of which are herein incorporated by reference.

BACKGROUND

1. Field of the Invention

The present invention relates to methods and systems for reducing artifacts in echo planar magnetic resonance imaging.

2. Description of the Related Art

Magnetic Resonance Imaging (MRI) is one of the most important modern medical imaging modalities. It has far less risk of side effects than most other imaging modalities such as radioscopy with x-rays or computed tomography because patients and medical personnel are not subjected to ionizing radiation exposure in the procedure. The use of MRI has grown very fast. Every year, more than 30 million MRI scans are performed in the United States; more than 60 million MRI scans are performed worldwide. Doctors often recommend MRI for the diagnosis of various diseases, such as tumors, strokes, heart problems, and spine diseases. A high-quality scan is important for maximizing diagnostic sensitivity and accuracy. Generally, high quality images are characterized by high signal to noise ratio (SNR), high contrast between normal and pathological tissues, low levels of artifacts, and appropriate spatial-temporal resolution In order to obtain a detectable MR signal, the object/subject examined is positioned in a homogeneous static magnetic field so that the object's nuclear spins generate net magnetization oriented along the static magnetic field. The net magnetization is rotated away from the static magnetic field using a radio frequency (RF) excitation field with the same frequency as the Larmor frequency of the nucleus. The angle of rotation is determined by the field strength of the RF excitation pulse and its duration. In the end of the RF excitation pulse, the nuclei, in relaxing to their normal spin conditions, generate a decaying signal (the "MR signal") at the same radio frequency as the RF excitation. The MR signal is picked up by a receive coil, amplified and processed. The acquired measurements, which are collected in the spatial frequency domain, are digitized and stored as complex numerical values in a "k-space" matrix. An associated MR image can be reconstructed from the k-space data, for example, by an inverse 2D or 3D fast Fourier transformation (FFT) from the raw k-space data.

Echo planar imaging ("EPI") is a fast imaging technique which can generate MR images at high temporal resolution, typically an image per tens micro-seconds. Therefore, it is widely used in diffusion imaging, for functional magnetic resonance imaging (fMRI), dynamic susceptibility contrast-enhanced (DSC) imaging, etc. However, EPI has several drawbacks, such as geometric distortions due to low bandwidth in the phase-encoding direction, image blurring due to $T^*_2$ relaxation, and signal dropouts due to magnetic susceptibility variations. Due to imperfections in the hardware system, such as eddy currents, delay in data acquisition, the nonuniformity of the basic magnetic field, Maxell effects, inconsistent magnetization, etc., the readout data under positive and negative frequency encoding gradients are not completely consistent. For example, there are cases such as the echo centers are inconsistent, the spacing between each line of the k-space is not equal, etc. Due to the mismatch of time or the phase differences between the odd and even echoes in an echo sequence, a low intensity overlapping image appears on a normal image after its reconstruction at a position half way offsetting an actual field of view (FOV), that is, the appearance of N/2 artifacts (also referred to as Nyqusit artifacts). In addition, due to the non-uniformity of the main magnetic field and the inconsistent magnetization, the odd and even echo signals cancel each other, leading to a signal loss in the reconstructed image. If the data sets are assembled into a complete data set without additional correction, the MR image data can have artifacts.

EPI suffers from two major sources of artifacts: N/2 or Nyquist ghosts, and geometric distortion which are caused by eddy current, Bo inhomogeneity, chemical shift and susceptibility. These factors lead to a mismatch between even and odd k-space data along phase encoding direction to create N/2 or Nyquist ghosts. Though an example method focuses on the correction of N/2 or Nyquist ghosts, the disclosed method and system can reduce the geometric distortion. In order to eliminate N/2 artifacts as much as possible, some correction methods, such as phase correction methods, unipolar readout gradient methods, post-processing methods, over-sampling methods, etc. So far, N/2 artifacts still affect the clinical practice of EPI sequence clinical practice. Numerous techniques for removing these artifacts have been disclosed in the following references:

U.S. Pat. No. 6,043,651 B2 to Oliver Heid discloses a method to correct N/2 artifacts in EPI. A phase correction data set is estimated from one echo or multiple echoes given a positive readout gradient to correct a data set from one echo or multiple echoes given a positive readout gradient. Similarly, an additional phase correction data set is estimated from one echo or multiple echoes given a negative readout gradient to correct an additional data set from one echo or multiple echoes given a negative readout gradient.

U.S. Pat. No. 7,772,847 B2 to Yuval Zur discloses method to correct Nyquist ghosting in single shot and multi-shot EPI scans by phase/magnitude correction in more than one direction. First, a phase/magnitude correction in the readout direction is carried out to reduce echo shifts and gradient waveform distortions. Then, a two dimensional phase/magnitude correction is performed to remove the remaining xy phase/magnitude errors.

U.S. Pat. No. 8,023,705 B2 to De He Weng and Wei Jun Zhang discloses method to correct Nyquist ghosting by over-sampling in the phase direction. The method includes acquiring multi-line k-space data; separating the multi-line k-space into odd line data and even line data; performing Fourier transform of the odd line data and the even line data separately; combining respective images for a final image.

U.S. Pat. No. 8,497,681 B2 to Thorsten Feiweier discloses a method and system for a phase correction in MR image data. The method includes acquiring first and second phase correction data sets; calculating correlations between data of the second phase correction data set and data of the first phase correction data set; determining phase correction parameters by phase curves of the second and first phase correction data sets.

International Application Publication No. WO2016180983A1 to Dimitrios Karampinos discloses method to correct the phase error using estimating accumulated concomitant gradient-induced phase error. The method includes reconstructing a complex MR image for each echo time from the echo signals generated at this echo time; computing the accumulated concomitant gradient-induced phase error for each echo time and for each image position from the gradient waveforms of the imaging sequence; and applying a phase correction to each voxel of each of the MR images.

U.S. Patent Application Publication No. 2017/0108571A1 to Michel Paul Jurriaan Jurrissen et al. discloses a method to correct EPI image artifacts of phase errors between odd and even k-space lines using a SENSE-type parallel imaging reconstruction in image domain. The method includes acquiring k-space along sets of lines in k-space along opposite propagation directions, e.g. odd and even lines in k-space; estimating the phase error distribution in image space using the phase difference between images reconstructed from magnetic resonance signals acquired from the respective sets of k-space lines, or from an earlier dynamic; correcting phase errors due to the opposite propagation directions are for in a SENSE-type parallel imaging reconstruction.

U.S. Patent Application Publication No. 2017/0307717 A1 to Benjamin J. Geraghty and Charles H. Cunningham discloses a method to correct off-resonance artifacts arising from the use of a multi-EPI pulse sequence using phase maps that are calculated in a distorted coordinate space associated with geometric distortions.

U.S. Patent Application Publication No. 2017/0089999A1 to Mario Zeller and Himanshu Bhat discloses a method to correct image artifacts caused by B0 drift and N/2 ghosting EPI with navigator-based correction of image data. The correction is based on two types of multi-echo phase-encoded navigator sequences having opposite readout gradient polarities, and optionally also uses a non-phase-encoded navigator sequence. A dynamic off-resonance in k-space technique can be used to correct for BO drift, and a modified slice GRAPPA technique that is based on odd and even kernels can provide slice-specific correction for N/2 ghosting effects for the EPI MR image data sets.

U.S. Pat. No. 9,612,307 B2 to Xiaohong Joe Zhou discloses a method to measure and correct for phase errors. The method including a spatially constant phase error and a spatially linear phase error from each of the reference scans for each relevant physical gradient axis; predicting the constant, linear, and oblique phase errors in each blade of an EPI PROPELLER k-space data set; producing an image with substantially reduced artifacts using the predicted these phase errors.

U.S. Pat. No. 9,880,247B2 to Lutfi Tugan Muftuleret al. discloses a method for reconstructing an image using highly accelerated projection imaging. The method includes acquiring k-space data with the MRI system along at least one trajectory; receiving an RF receive coil sensitivity map for each RF coil; producing at least one projection by performing a one-dimensional Fourier transform on the k-space data sampled; determining a plurality of weights, each weight being determined by calculating an overlap of a ray corresponding to the at least one projection and a voxel at a voxel location in an image matrix; forming a matrix; and reconstructing the image using the formed matrix.

U.S. Pat. No. 9,886,745B2 to Nan-kuei Chen, Allen W. Song discloses a method to improve image quality of multi-shot diffusion weighted imaging using multiplexed sensitivity-encoding (MUSE) without requiring the use of navigator echoes. This new technique can provide highly valuable technique for brain structures and connectivity at high spatial resolution.

U.S. Patent Application Publication No. 2018/0238986A1 to Elwin De Weerdt and Zhaolin Chen discloses a method to correct the Nyquist ghost artifacts. The method mainly includes: reconstructing a complex MR image for each echo time from the echo signals generated at this echo time; computing the accumulated concomitant gradient-induced phase error for each echo time and for each image position from the gradient waveforms of the imaging sequence; and applying a phase correction to each voxel of each of the MR images according to the computed accumulated concomitant gradient-induced phase error for the respective echo time and image position.

U.S. Pat. No. 9,989,606B2 to David Leslie Foxall discloses a method to correct Nyquist ghosting for both single-shot and multi-shot EPI acquisitions. The method includes acquiring a dynamic series of nominally identical dynamic image datasets, each image dataset comprising multiple shots of imaging data acquired using a magnetic resonance imaging (MRI) scanner; normalizing the signal power of each shot of an image dataset of the image datasets to a reference signal power to generate a power-normalized shot representation having total signal power matching the reference signal power; and generating a reconstructed image from the power-normalized shot representations.

U.S. Pat. No. 9,933,505B2 to James Grant Pipe discloses systems and methods for estimating bulk rotation and translation of an imaged subject for a PROPELLER MRI or similar sequence.

U.S. Patent Application Publication No. 2018/0335495A1 to Jeff Alan Stainsby and Chad Tyler Harris disclose a method to correct image artifacts caused by eddy current using adjusting amplitude and phase of current of gradient coils. That is, they correct the eddy current artifacts by the adjustment of hardware.

These conventional methods try to find the relationship between k-space lines corresponding to even and odd echoes and correct a mismatch of both even and odd k-space data along phase encoding direction to reduce N/2 or Nyquist ghosts. MRI system is very complex, and the mismatch between even and odd k-space data along phase encoding direction to reduce N/2 or Nyquist ghosts may vary over time. It is very difficult to estimate exact and robust mismatch. A need persists in the art for a method of correcting N/2 or Nyquist ghost artifacts in echo planar imaging.

SUMMARY

An object of the present disclosure is to provide a method for correcting Nyquist ghost or N/2 ghost of an image acquired with echo planar imaging.

Numerous methods have been proposed to correct Nyquist ghost or N/2 ghost using phase variation. In general, these methods can be divided into two groups: model-based methods and non-model-based on methods. As for model-based methods, the phase error is usually modeled as either one-dimensional (1D) or two-dimensional 2D phase error which can be estimated and modeled from a reference scan or image based entropy optimization because eddy current and magnetic susceptibility effect can introduce high-order phase errors. Additionally, the k-space difference between add and even k-space line is not only translational but also rotational. The phase variation only relates to the translation motion of object being imaged by MRI system. Therefore, it is not enough that only phase variation is used to correct N/2 ghost or Nyquist artifacts.

In one embodiment, a method for reducing N/2 ghost or Nyquist ghost in magnetic resonance (MR) images is provided The method includes acquiring k-space dataset for an object using an echo planar imaging (EPI) sequence, dividing the k-space dataset into first partial k-space subset data related to positive echoes and second partial k-space subset data related to negative echoes, obtaining third partial k-space subset data that is N/2 ghost-free or Nyquist ghost-free subset data, respectively registering the first partial k-space subset data and the second partial k-space subset data to a first portion of the third partial k-space subset data corresponding to positive echoes and a second portion of the third partial k-space subset data corresponding to negative echoes, combining the registered first partial k-space subset data and the second partial k-space subset data to form full k-space dataset, and reconstructing an image for the object based on the full k-space dataset.

In another embodiment, a method for reducing N/2 ghost or Nyquist ghost in magnetic resonance (MR) images is provided. The method includes acquiring k-space dataset for an object using an echo planar imaging (EPI) sequence, dividing the k-space dataset into first partial k-space subset data related to even echoes and second partial k-space subset data related to odd echoes, obtaining third partial k-space subset data that is N/2 ghost-free or Nyquist ghost-free subset data, estimating relational information between each even k-space data and odd k-space data adjacent to the each odd k-space data based on the ghost-free reference k-space dataset, estimating another relational information between each odd k-space data and even k-space data adjacent to the each even k-space data based on the ghost-free reference k-space dataset, synthesizing missing k-space lines related to odd echoes in the first partial k-space subset data based on the first partial k-space subset data and the relational information, synthesizing missing k-space lines related to even echoes in the second partial k-space subset data based on the second partial k-space subset data and the another relational information, creating a first full k-space dataset related to both odd and even echoes by combining the first partial k-space subset data and the synthesized k-space lines related to odd echoes, creating a second full k-space dataset related to both odd and even echoes by combining the second partial k-space subset data and the synthesized k-space lines related to even echoes, reconstructing a first ghost-free EPI image from the first full k-space dataset, reconstructing a second ghost-free EPI images from the second full k-space dataset, and creating a ghost-free EPI image using the first and second ghost-free EPI images.

In yet another embodiments, a magnetic resonance imaging (MRI) system is provided. The MRI system includes, a magnetic field generating unit configured to apply a plurality of RF pulses with a variable flip angle to a target area in the object, a receiver configured to receive MR signals from the target area, a processing unit, a system memory, and machine readable instructions stored in the system memory. The machine readable instructions, when executed by the processing unit, cause the processing unit to: acquire k-space dataset for an object using an echo planar imaging (EPI) sequence; divide the k-space dataset into first partial k-space subset data related to positive echoes and second partial k-space subset data related to negative echoes; obtain third partial k-space subset data that is N/2 or Nyquist ghost-free subset data; respectively register the first partial k-space subset data and the second partial k-space subset data to a first portion of the third partial k-space subset data corresponding to positive echoes and a second portion of the third partial k-space subset data corresponding to negative echoes; combine the registered first partial k-space subset data and the registered second partial k-space subset data to form full k-space dataset; and reconstruct an image for the object based on the full k-space dataset.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIG. 9A is a graph illustrating an example single-shot echo-planar imaging sequence configuration for an image acquired with non-uniform phase encoding according to one example in the present disclosure.

DETAILED DESCRIPTION

1. Definition

Figure 1:
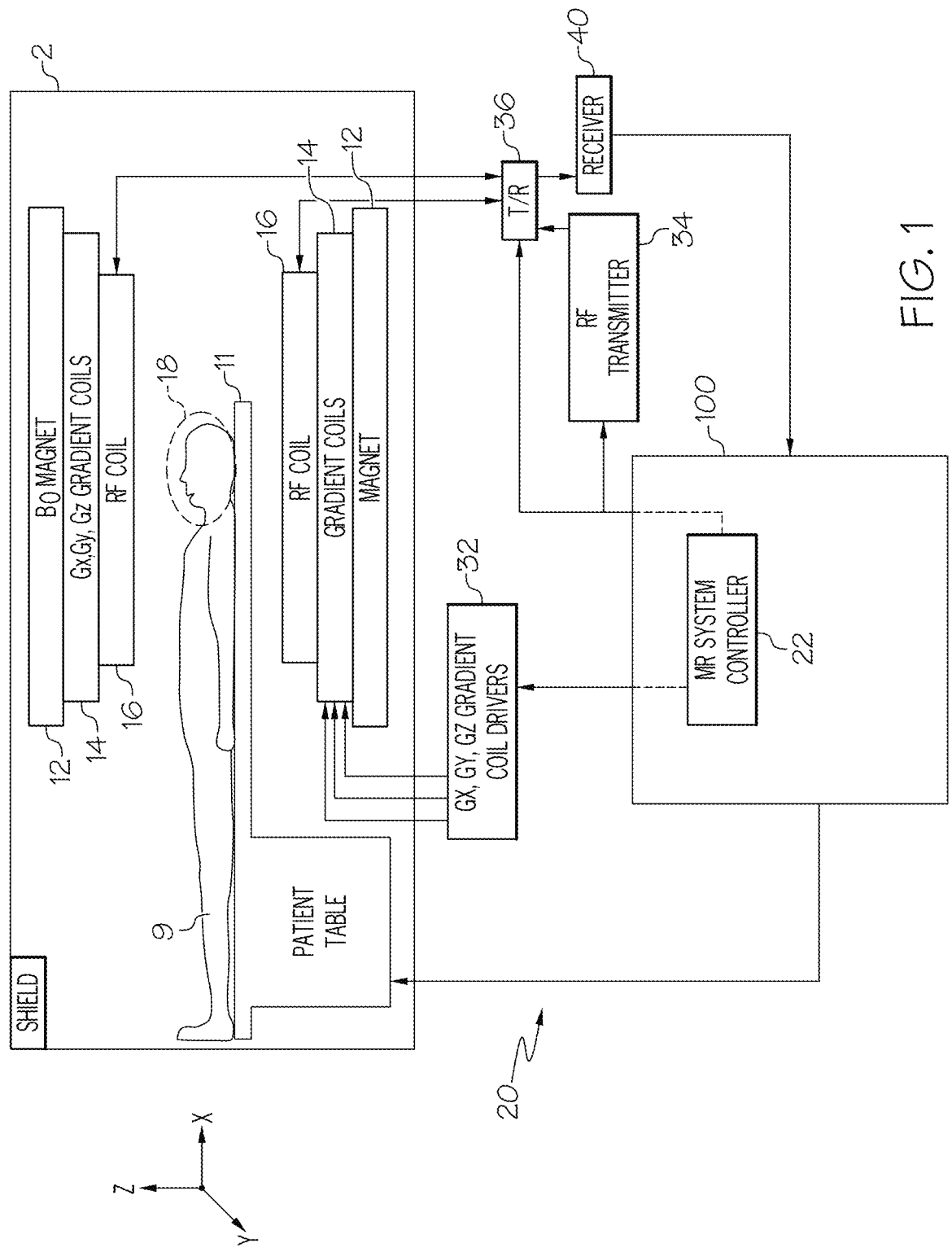
FIG. 1 is a diagram illustrating an example MRI system.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. While implementations will be described for optimizing MRI scanner settings (also referred to herein as "basic scanner settings"), MRI protocols, variable flip angle, k-space strategy, and/or imaging parameters with regard to MRI modalities, it will become evident to those skilled in the art that the implementations are not limited thereto, but are applicable to other image modalities such as, computed tomography, for example. Additionally, this disclosure contemplates that MRI modalities include MRI techniques with administration of contrast agents, for example, contrast enhanced MR angiography. This disclosure contemplates that the images obtained using the techniques described herein can be directly employed in at least one of diagnosing diseases, monitoring prognosis and therapeutic responses, conducting treatment plans, and improving quantification of MRI. For example, the techniques described herein can be used for the diagnoses of specific diseases such as the standardization of the MRI protocol in The Alzheimer's Disease Neuroimaging Initiative. Additionally, the techniques described herein are optionally applicable to a group of individuals in a similar pathophysiological situation.

The term "each acquisition" and variations thereof as used herein is used synonymously with the term "each k-space line" or "each phase-encoding" or " each readout radiofrequency pulse" or "each echo" or " each readout gradient pulse" and variations thereof and are open, non-limiting terms.

The term "k-space" and variations (such as frequency domain or raw data) thereof as used herein indicate the data space in which MRI raw data is acquired. The k-space represents the spatial frequency information in two or three dimensions of an object. The k-space is defined as a space covered by the phase and frequency encoding data. In contrast to this, the Fourier-transformed counterpart of the k-space is defined as an image space or image domain. The relationship between k-space data and image data is the Fourier transformation. Each data point in k-space represents a different superposition of the tissue signals. Every point in the raw data matrix contains part of the information for the complete image. A point in the raw data matrix does not correspond to a point in the image matrix. The high spatial frequency components provide information about the borders and contours of the image, the detail of the structures. The low spatial frequency components provide information on the general contrast of the image.

The term "k-space trajectory" and variations thereof as used herein indicate the path traced in k-space domain during MRI data collection. The k-space trajectory is used to illustrate the acquisition strategy. It has great influences on artifacts and the image reconstruction.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation.

The term "reconstructing image" and variations thereof as used herein indicate a process for transforming the acquired k-space data (e.g. raw data) into images.

The term "functional system" and variations thereof as used herein include, but are not limited to hardware, software to perform a function and/or an action.

The term "reconstruction" and variations thereof as used herein indicate a mathematical process that generates MRI images from incomplete raw data acquired at many different conditions to improve image quality and reduce the artefacts.

The term "N/2 ghost or Nyquist ghost artifact" and variations thereof as used herein indicate that a severe artefact is observed in echo planar images (single shot or multiple shot EPI). The Nyquist ghost is caused by the asymmetries or inconsistencies between the odd and even k-space lines occurring due to positive and negative gradient pulses of the alternating readout gradient pulse trains. The ghost image shifted by half the field of view in the phase-encoding direction of the image.

2. MRI System Overview

FIG. 1 depicts an MRI system 10, according to one or more embodiments described and shown herewith. In embodiments, the MRI system 10 shown in FIG. 1 includes a patient table 11, a static magnetic field generating unit 12, a gradient magnetic field generating unit 14 for generating respective magnetic fields in proximity to a target area 18 of an object 9, a transmitting and receiving unit 16, and a computing device 100. The patient table 11, the static magnetic field generating unit 12, the gradient magnetic field generating unit 14, and the transmitting and receiving unit 16 are placed within MRI RF shielding area 2 where noise of radio frequency is prevented from entering.

The static magnetic field generating unit 12 includes a main magnet configured to generate a strong static magnetic field in proximity to the target area 18 of the object 9. The static magnetic field generating unit 12 may be arranged to surround the target area 18 of the object 9. For example, the static magnetic field generating unit 12 may be a cylindrical-shaped unit. The gradient magnetic field generating unit 14 includes gradient magnetic field coils for generating gradient magnetic fields in an x-axis direction, a y-axis direction, and a z-axis direction, which are orthogonal to each other. The gradient magnetic field generating unit 14 may be arranged to surround the target area 18 of the object 9. For example, the gradient magnetic field generating unit 14 may be a cylindrical-shaped unit.

In embodiments, the transmitting and receiving unit 16 may include a transmission coil and a receiving coil. The transmission coil irradiates RF pulses to the object 9 and the receiving coil receives MR signals generated by the object 9. In some embodiments, the transmitting and receiving unit 16 may include a transceiver coil having the functions of both the transmission coil and the receiving coil. The receiving coil may be composed of, for example, a so-called array coil in which, for example, a plurality of coil elements are disposed to detect the MR signals generated by the object 9. An RF transmitter 34 may control the transmission coil of the transmitting and receiving unit 16 to irradiate RF pulses. A receiver 40 may receive MR signals generated by the object 9 from the receiving coil of the transmission and receiving unit 16. The RF transmitter 34 and the receiver 40 may communicate with the transmitting and receiving unit 16 through a transmitter/receiver interface 36.

In embodiments, the MRI system 10 includes the computing device 100. The computing device 100 includes a MRI system controller 22. The MRI system controller 22 may control the operations of the gradient coil drivers 32 that activate the gradient coils of the gradient magnetic field generating unit 14. The MRI system controller 22 may also control the operations of the RF transmitter 34 that activates the RF coil of the static magnetic field generating unit 12. The computing device 100 may receive MR signals from the receiving coil of the transmission and receiving unit 16 and reconstruct an MRI image based on the received MR signals. The details of the computing device 100 will be further described with reference to FIG. 1A below.

In embodiment, the computing device 100 may be operably coupled to other components of the MRI system 10, for example, using by any medium that facilitates data exchange between the components of the MRI system 10 and the computing device 100 including, but not limited to, wired, wireless and optical links. For example, the computing device 100 may convert the MR signals received from the transmitting and receiving unit 16 into k-space data. The computing device 100 may generate MR image data from the k-space data with image reconstruction processing. In some embodiments, the techniques for improving image quality with optimal variable flip angles may optionally be implemented using the MRI system 10.

3. Example Computing Device

Figure 1A:
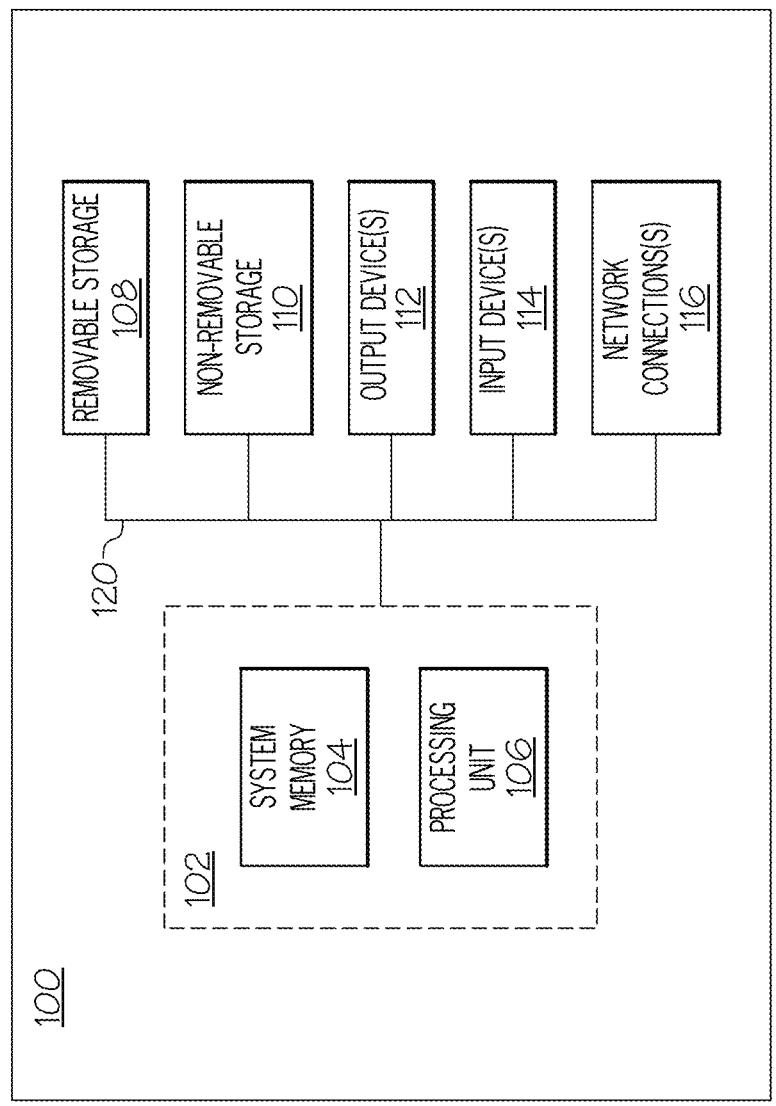
FIG. 1A is an example computing device.

FIG. 1A depicts a computing device 100 according to one or more embodiments shown and described herein. It should be appreciated that the logical operations described herein with respect to the various figures may be implemented (1) as a sequence of computer implemented acts or program modules (i.e., software) running on a computing device (e.g., the computing device described in FIG. 1A), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

It should be understood that the computing device 100 is only one example of a suitable computing environment upon which embodiments of the invention may be implemented. Optionally, the computing device 100 may be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In embodiments, the computing device 100 includes a controller 102 that includes one or more processing units 106 and one or more system memory modules 104. The controller 102 may be the same controller as the MRI system controller 22 in FIG. 1. In other embodiments, the controller 102 may be a separate controller from the MRI system controller 22 in FIG. 1. Depending on the exact configuration and type of computing device, the one or more memory modules 104 may be volatile (such as random access memory (RAM)), non-volatile (such as read-only memory (ROM), flash memory, etc.), or some combination of the two. The one or more processing units 106 may be a standard programmable processor that performs arithmetic and logic operations necessary for operation of the computing device 100.

In embodiments, the computing device 100 includes communication path 120 that provides signal interconnectivity between various components of the computing device 100. Accordingly, the communication path 120 may communicatively couple any number of processing units 106 with one another, and allow the components coupled to the communication path 120 to operate in a distributed computing environment. Specifically, each of the components may operate as a node that may send and/or receive data. As used herein, the term "communicatively coupled" means that coupled components are capable of exchanging data signals with one another such as, for example, electrical signals via conductive medium, electromagnetic signals via air, optical signals via optical waveguides, and the like.

Accordingly, the communication path 120 may be formed from any medium that is capable of transmitting a signal such as, for example, conductive wires, conductive traces, optical waveguides, or the like. In some embodiments, the communication path 120 may facilitate the transmission of wireless signals, such as Wi-Fi, Bluetooth, Near Field Communication (NFC) and the like. Moreover, the communication path 120 may be formed from a combination of mediums capable of transmitting signals. In one embodiment, the communication path 120 comprises a combination of conductive traces, conductive wires, connectors, and buses that cooperate to permit the transmission of electrical data signals to components such as processors, memories, sensors, input devices, output devices, and communication devices. Accordingly, the communication path 120 may comprise a vehicle bus, such as for example a LIN bus, a CAN bus, a VAN bus, and the like. Additionally, it is noted that the term "signal" means a waveform (e.g., electrical, optical, magnetic, mechanical or electromagnetic), such as DC, AC, sinusoidal-wave, triangular-wave, square-wave, vibration, and the like, capable of traveling through a medium.

The one or more processing units 106 may be configured to execute program code encoded in tangible, computer-readable media. Tangible, computer-readable media refers to any media that is capable of providing data that causes the computing device 100 (i.e., a machine) to operate in a particular fashion. Various computer-readable media may be utilized to provide instructions to the one or more processing units 106 for execution. Example tangible, computer-readable media may include, but is not limited to, volatile media, non-volatile media, removable media and non-removable media implemented in any method or technology for storage of information such as computer readable instructions, data structures, program modules or other data. One or more system memory modules 104, a removable storage 108, and a non-removable storage 110 are all examples of tangible, computer storage media. Tangible, computer-readable recording media may include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In embodiments, the one or more processing units 106 may execute program code stored in the one or more system memory modules 104. For example, a bus may carry data to the one or more system memory modules 104, from which the one or more processing units 106 receive and execute instructions. The data received by the one or more system memory modules 104 may be optionally stored on the removable storage 108 or the non-removable storage 110 before or after execution by the processing unit 106.

In embodiments, the computing device 100 may include additional storage such as removable storage 108 and non-removable storage 110 including, but not limited to, magnetic or optical disks or tapes.

The computing device 100 may also have input device(s) 114 such as a keyboard, mouse, touch screen, etc. The input device may be manipulated by an operator to input signals to the MRI apparatus to set the imaging method group, the performing order, the imaging condition, and the like. The computing device 100 may also have output device(s) 112 such as a display, speakers, printer, etc. The output device 112 may output image data such as local image data, diagnosis image data using display, printer and other displayer. The additional devices may be connected to the bus in order to facilitate communication of data among the components of the computing device 100.

Computing device 100 may also contain network connection(s) 116 that allow the device to communicate with other devices. The network connection(s) 116 may be any device capable of transmitting and/or receiving data via a wireless network. Accordingly, the network connection(s) 116 may include a communication transceiver for sending and/or receiving data according to any wireless communication standard. For example, the network connection(s) 116 may include a chipset (e.g., antenna, processors, machine readable instructions, etc.) to communicate over wireless computer networks such as, for example, wireless fidelity (Wi-Fi), WiMax, Bluetooth, IrDA, Wireless USB, Z-Wave, ZigBee, or the like.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

In some embodiments, the computing device 100 may include a workflow setting unit, an imaging operation determining unit, and an image reconstruction unit. The workflow setting unit may be a program module stored in the system memory modules 104. The workflow setting unit sets a first workflow relating to the MRI examination by estimating an imaging time of each of the imaging methods in the performing order initially set by a scan plan. Further, the workflow setting unit sets a second workflow relating to the MRI examination by estimating a shortest performing order, by which an examination time necessary to sequentially perform a plurality of imaging methods constituting the imaging method group set by, the input unit is minimized. The imaging operation determining unit determines whether an imaging operation during a main imaging is implemented according to the workflow. In embodiments, the workflow setting unit and/or the imaging operation unit may be implemented using hardware, software, and or a combination thereof.

The image reconstruction unit may include an MR signal storage unit, a signal processing unit, and an image data storage unit. The MR signal storage unit (e.g., memory) stores the MR signals, which are collected by the receiver unit of the transmitting and receiving unit 16. The signal processing unit has an image reconstruction processing unit and an image processing unit. The image reconstruction processing unit generates image data from the MR signal storage unit by image reconstruction processing, for example, performed by a Fourier transformation such as 2D FFT. When the MR signals to a three-dimensional region are collected, the image reconstruction processing unit of the signal processing unit generates volume data. Subsequently, the image processing unit generates three-dimensional image data such as volume rendering image data, surface rendering image data and the like or two-dimensional image data, multi planar reconstruction image data, and the like, because predetermined image processing is performed for the volume data generated by the image reconstruction processing unit. Then, the image data described above obtained by the signal processing unit are stored to the respective storage regions of the image data storage unit.

4. Overview

One of the most successful technical developments to fast MRI scan time in the last 40 years was echo planar imaging (EPI). EPI is based on rapid sequence as a plurality of gradient echoes in the readout phase, with a rapid changing of the polarity of a readout gradient for successive echo signals. The alternating polarity of the readout gradients result in raw image data that fills lines in k-space in alternate directions positive and negative echoes. The eddy currents, imperfect gradients, and timing errors can cause inconsistencies between k-space lines of opposite polarity (e.g. or positive and negative echoes), leading to an artifact known as N/2 ghost or Nyquist ghost.

Numerous techniques have been developed for removing N/2 ghost artifacts. These methods can be divided into two categories: reference-based approaches and reference-free methods. The reference based method uses additional pre-scan or reference scan to estimate the difference of even and odd echoes, and then corrects the inconsistency of even and odd echoes after data acquisition. Since it takes too much time to obtain a full reference scan, most techniques usually acquired several echoes in practice. However, the reference method still has additional time for acquiring the reference echoes. Conversely, reference free methods correct ghost artifacts using a pulse sequence compensation or modification during data acquisition. In these methods, ghost artifacts are removed by editing a puke sequence, from which two images are obtained, and one can estimate the compensation factor between two ghosts. For example, small blips gradient is added on the phase encoding direction of the conventional EPI sequence to compensate the inconsistency of even and odd echoes. N/2 ghost problem is regarded as a parallel acquisition problem with the acceleration factors of 2 because their artifacts patterns is very similar. The existing parallel image reconstruction methods, such as SENSE (Sensitivity encoding) and GRAPPA, can be used to conduct the correction of N/2 ghost. Even though these method showed improved quality of EPI images, they still suffered from intrinsic problems of parallel imaging reconstructions, such as accurate estimation of coil sensitivity.

Two k-spaces (echoes) may be acquired under the positive and negative readout lobes, respectively, by performing phase encoding blips only before alternate readout gradients. The two entirely ghost free images per shot may be constructed, without need for phase correction. In this disclosure, non-uniform phase encoding may apply in the central k-space. That is, positive and negative readout lobes are conducted at each central k-space line. The central k-space line is ghost free and is used to correct even and odd k-space lines at peripheral k-space.

Conventional reference-based methods may address Nyquist ghost when the ghosting causes the shifting of even and odd echoes due to imperfect timing in the pulse sequence. The phase error is a good approximation to describe the inconsistency of the even and odd echoes. However, in the presence of strong Bo inhomogeneity, eddy current, susceptibility, chemical shift and other off-resonance effects, conventional reference-based method may not always sufficiently reduce image artifacts. The conventional methods do not take into account distortions of the echo signal, and thus does not suppress the ghosts. It may be necessary to use higher-order correction because a small number of cases none of the ghost correction methods fully suppressed the ghost. High-order phase errors along both readout and phase-encoding directions may be corrected and artifact-free EPI may be reconstructed. The implicit assumption is a constant odd-even offset along the readout. The strong eddy current and other off-resonance effects can cause the inconsistency of even and odd k-space lines during echo planar imaging in both translation and rotation, even shearing. Dealing with translation only is not enough to correct the image artifacts. In this present disclosure, k-space registration is introduced to correct the N/2 ghost and other artifacts to overcome the shortcoming of phase correction.

Most recently, the paper "Scan-specific robust artificial-neural-networks for k-space interpolation (RAKI) re-construction: Database-free deep learning for fast imaging." in Magnetic Resonance in Medicine. 2019;81(1): 439-453 to Akcakaya M et al. disclosed Robust artificial-neural-networks for k-space interpolation (RAKI) method for improved k-space interpolation using a scan-specific machine learning approach . The method uses scan-specific autocalibration signal (ACS) lines to train neural networks for interpolation. Missing k-space points are estimated from k-space data acquired with multiple array coils. As a result, this method may introduce the correlation between each multiple array coil, and then cause the artifacts and amplify the noise.

Figure 2:
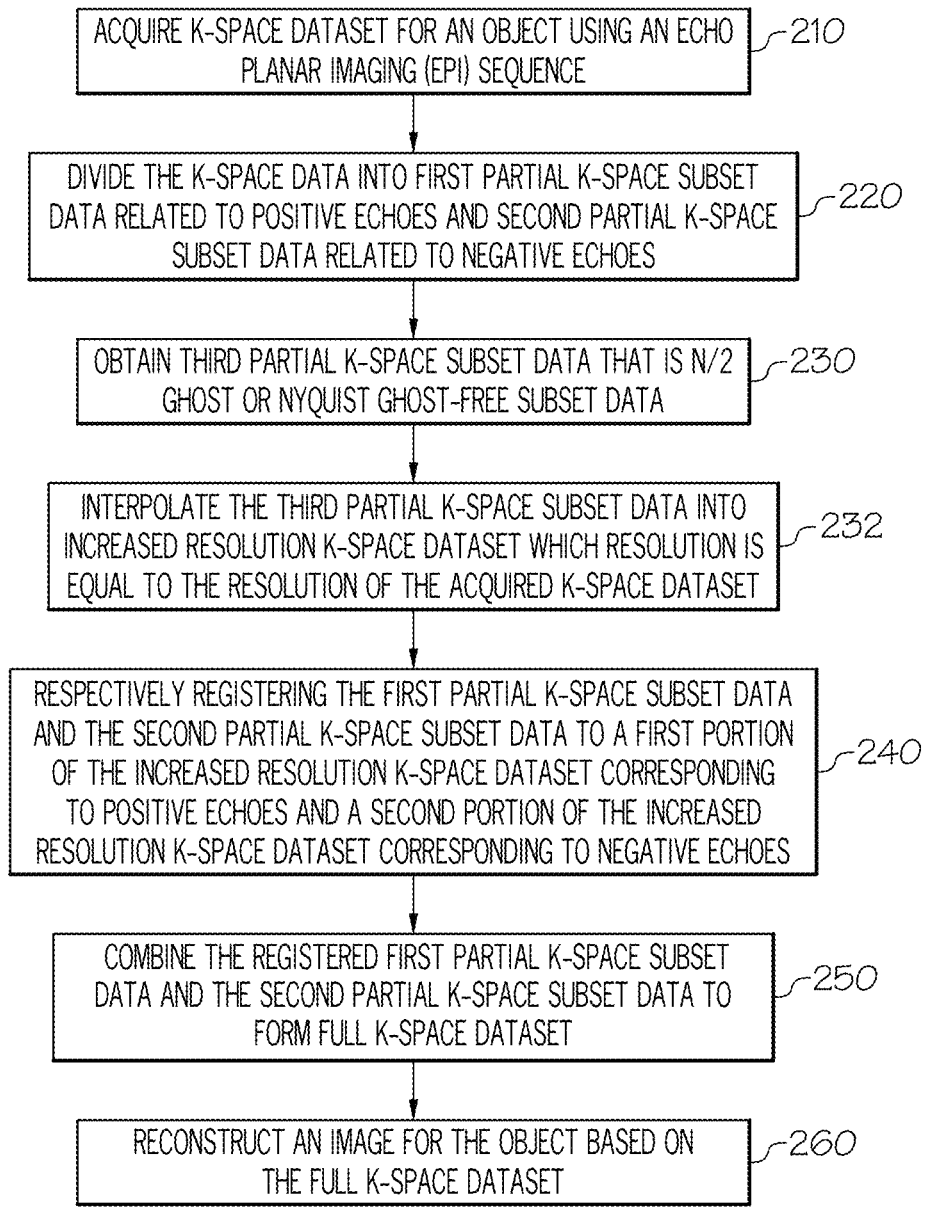
FIG. 2 is a flowchart for reducing N/2 ghost or Nyquist ghost of an image acquired with echo planar imaging technique according to one example in the present disclosure.

FIG. 2 is a flowchart for reducing N/2 ghost or Nyquist ghost of an image acquired with echo planar imaging technique according to one example in the present disclosure.

Figure 3:
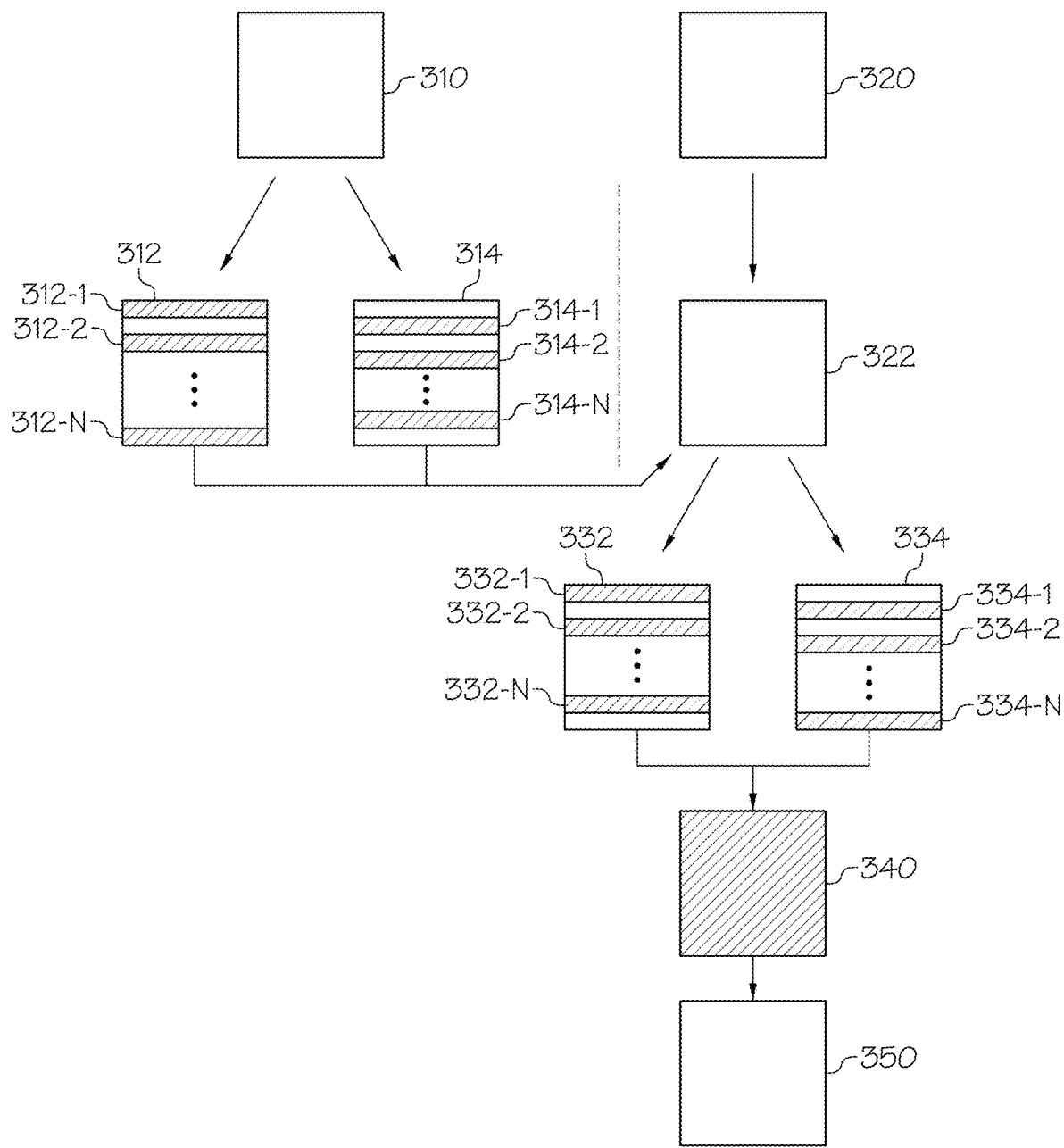
FIG. 3 schematically depicts an example operation for reducing N/2 ghost or Nyquist ghost of an image acquired with echo planar imaging technique, according to one example in the present disclosure.

In step 210, the computing device 100 acquires k-space dataset for an object using an echo planar imaging (EPI) sequence. In embodiments, as shown in FIG. 1, the computing device 100 receives MR signals from the transmitting and receiving unit 16 and acquires a k-space dataset for the object 9. For example, the k-space dataset 310 in FIG. 3 may be acquired. The echo planar imaging sequence may be either single-shot or multi-shots.

In embodiments, the k-space dataset may be acquired in phase-encoding directions. In some embodiments, the k-space dataset is acquired in frequency-encoding directions. In some embodiments, the k-space dataset may be acquired using a combination of partial Fourier acquisition and other under-sampling techniques, such as compressed sensing and parallel imaging acquisitions.

In embodiments, the k-space dataset may be acquired with at least one of $T_1$-weighted spin echo, $T_2$-weighted spin echo, fluid-attenuated inversion-recovery, $T_1$-weighted gradient-echo, $T_2^*$-weighted gradient echo, contrast enhanced $T_1$-weighted gradient echo, contrast enhanced $T_1$-weighted spin echo, diffusion-weighted spin echo, and their variations or combinations.

In embodiments, the k-space dataset may be acquired with imaging sequence including, but not limited to, at least one of two spatial dimensional, three spatial dimensional, or three spatial dimensional plus temporal image acquisition. In some embodiments, the imaging sequence may include at least one of a gradient echo, echo planar or spin echo sequence with or without magnetization preparation, with or without under-sampling techniques, with or without parallel imaging techniques, or with or without Cartesian k-space trajectories. The imaging sequence can include at least one of two spatial dimensional, three spatial dimensional, or three spatial dimensional plus temporal image acquisition. For example, dynamic contrast agent enhanced imaging and blood oxygen level dependent functional MRI may deal with motion at the different time frames.

In embodiments, the k-space dataset may be acquired using k-space trajectory including at least one of rectilinear, echo planar, but not limited to, radial, Cartesian, non-Cartesian, Zig-Zag, stochastic, rosette, TWIRL, WHIRL and spiral trajectories. The k-space dataset may be acquired according to a k-space sampling order including at least one of a sequential sampling order, a centric sampling order, an interleave sampling order, a reverse sampling order, a random sampling order, or a hybrid sampling order.

In embodiments, the computing device 100 acquires a k-space dataset for a region of interest using an MR scanner. The region of interest may include at least a portion of a subject's body with or without disease. The portion of the subject's body may be at least one of an extremity, brain, spine, neck, chest, breast, joint, prostate, pelvis, or abdomen.

In step 220, the computing device 100 divides the k-space dataset into first partial k-space subset data related to positive echoes and second partial k-space subset data related to negative echoes. By referring to FIG. 3, in embodiments, the computing device 100 divides the k-space dataset 310 into first partial k-space subset data 312 related to positive echoes and second partial k-space subset data 314 related to negative echoes. The first partial k-space subset data 312 includes k-space lines 312-1 through 312-N related to positive echoes. The second partial k-space subset data 314 includes k-space lines 314-1 through 314-N related to negative echoes.

In step 230, the computing device 100 obtains third partial k-space subset data that is N/2 ghost-free or Nyquist ghost-free subset data. In embodiments, the computing device 100 obtains the third partial k-space subset data 320 illustrated in FIG. 3. For example, the third partial k-space subset data 320 may be obtained from the acquired k-space dataset 310. As another example, the third partial k-space subset data 320 may be obtained from additional MR scanning. In embodiments, the k-space dataset 310 is acquired using non-uniform phase encoding, and the third partial k-space subset data is obtained from the k-space dataset 310 acquired using the non-uniform phase encoding. In some embodiments, the third partial k-space subset data 320 may be acquired by the EPI sequence at a time frame different from a time frame when the first partial k-space subset data 312 and the second partial k-space subset data 314 are acquired. In some embodiments, the third partial k-space subset data 320 may be acquired by another EPI sequence different from the EPI sequence used for the k-space dataset 310, and the third partial k-space subset data 320 and the first and second partial k-space subset data 312 and 314 are acquired at a same modality or different modalities. The different modalities can include CT, but are not limited to, PET. The same modality may include conventional gradient echo sequence, spin echo sequence, but is not limited to, fast spin echo sequence.

In embodiment, the Nyquist ghost-free subset data may be acquired with EPI sequence. For example, the Nyquist ghost-free subset data may be conducted interleaved dual echo with acceleration EPI. This method almost doubles the total scan time, and reduces temporal resolution. This limits the application of the proposed method in fMRI and diffusion weighted imaging. EPI acquisition with non-uniform phase encoding may address the issue. As another example, the Nyquist ghost-free subset data may be provided by images which have been acquired by conventional MRI sequences in routine clinical practice and research. For example, $T_1$-weighted and $T_2$-weighted images are often acquired before EPI sequences as a reference for position. As another example, a low spatial resolution image may be acquired by conventional gradient echo and fast spin echo as the Nyquist ghost-free subset data.

Figure 7:
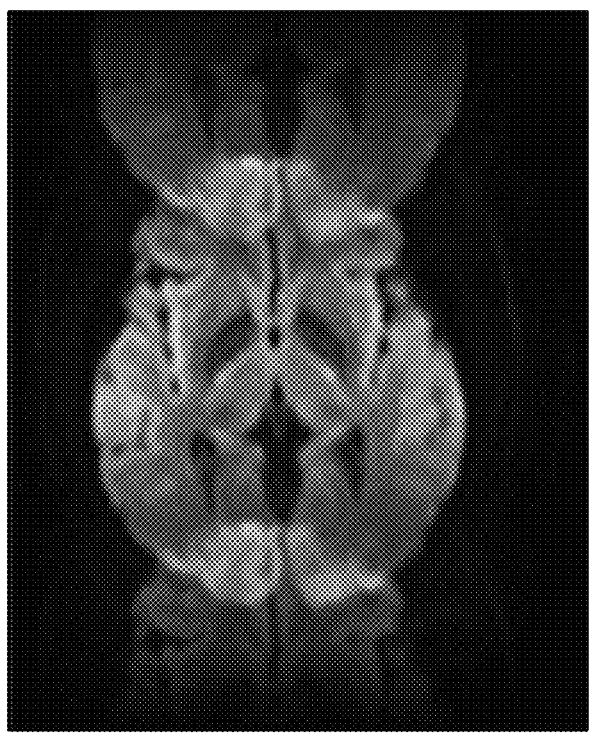
FIG. 7 illustrates an exemplary brain image acquired with single-shot spin-echo echo planar imaging technique.

An image with lower spatial resolution compared to the image acquired by EPI technique may be acquired with the same EPI sequence or conventional gradient echo sequence without Nyquist ghost. The k-space data of this image may be used as a reference to correct the k-space variation of even and odd echoes mainly caused by positive and negative readout gradient polarities. FIG. 7 illustrates an exemplary brain image acquired with single-shot spin-echo echo planar imaging technique according to one example in the present disclosure. The apparent N/2 ghost or Nyquist ghost is observed, leading to the significant reduction of image quality. Conventional EPI sequence, either positive or negative echo, may acquire at each phase encoding step. An image with lower spatial resolution may be acquired with conventional gradient echo. The k-space data corresponding to the image with lower spatial resolution may be regarded as the third partial k-space subset data. When the effect caused by eddy current and $B_0$ inhomogeneity, etc. on k-space variation is assumed to be identical for the central and peripheral k-space data, the peripheral k-space data with Nyquist ghost can be corrected by the transformation matrix which is estimated by the corresponding entire or part of central k-space data of both positive and negative echoes without Nyquist ghost, as described below with reference to FIGS. 3 and 4.

In step 232, the computing device 100 interpolates the third partial k-space subset data into increased resolution k-space dataset which resolution is equal to the resolution of the acquired k-space dataset. In embodiments, by referring to FIG. 3, the third partial k-space subset data 320 may be acquired with relatively low resolution without Nyquist ghost. The computing device 100 may interpolate the third partial k-space subset data 320 to obtain increased resolution k-space dataset 322 which resolution is equal to the resolution of the acquired k-space dataset 310.

In step 240, the computing device 100 respectively registers the first partial k-space subset data and the second partial k-space subset data to a first portion of the increased resolution k-space dataset corresponding to positive echoes and a second portion of the increased resolution k-space dataset corresponding to negative echoes. By referring to FIG. 3, the first partial k-space subset data 312 is registered to a first portion of the increased resolution k-space dataset 322 corresponding to the positive echoes. The second partial k-space subset data 314 is registered to a second portion of the increased resolution k-space dataset 322 corresponding to the negative echoes.

Figures 4A, 4B:
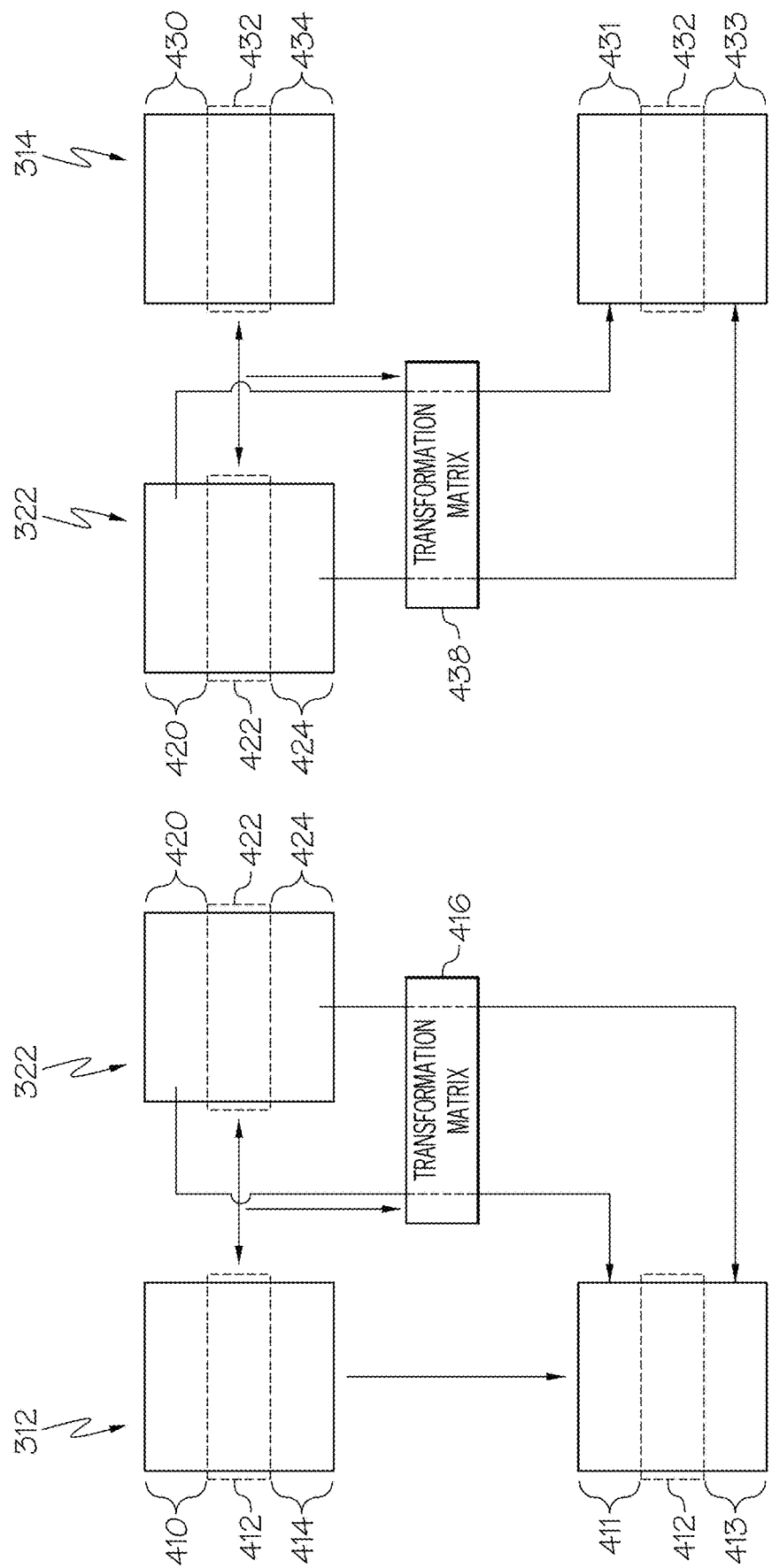
FIG. 4A schematically depicts an example operation for registering first partial k-space subset data to a Nyquest ghost-free data, according to one example in the present disclosure.
FIG. 4B schematically depicts an example operation for registering second partial k-space subset data to a Nyquest ghost-free data, according to one example in the present disclosure.

In embodiments, registering the first partial k-space subset data and the second partial k-space subset data to the increased resolution k-space dataset is illustrated in FIGS. 4A and 4B. The computing device 100 may estimate a first transformation matrix 416 based on the first partial k-space subset data and the increased resolution k-space dataset corresponding to the first partial k-space subset data. The first partial k-space subset data 312 may include k-space data 410, k-space data 412, and k-space data 414. The k-space data 410 and the k-space data 414 may include Nyquist ghost, and the k-space data 412 may not include Nyquist ghost. The increased resolution k-space dataset 322 may include k-space data 420 corresponding to the k-space data 410, k-space data 422 corresponding to the k-space data 412, and k-space data 424 corresponding to the k-space data 414. The computing device 100 may estimate a first transformation matrix 416 based on the k-space data 412 and the k-space data 424. The transformation matrix reflects the variations of translation, rotation, and/or shear data of k-space data between two sets of k-space data. The first transformation matrix 416 may receive the k-space data 424 as an input and output the k-space data 412 as an output.

Then, the computing device 100 estimates a second transformation matrix 438 based on the second partial k-space subset data and the increased resolution k-space dataset corresponding to the second partial k-space subset data. The second partial k-space subset data 314 may include k-space data 430, k-space data 432, and k-space data 434. The k-space data 430 and the k-space data 434 may include Nyquist ghost, and the k-space data 432 may not include Nyquist ghost. The increased resolution k-space dataset 322 may include k-space data 420 corresponding to the k-space data 430, k-space data 422 corresponding to the k-space data 432, and k-space data 424 corresponding to the k-space data 434. The computing device 410 may estimate a second transformation matrix 438 based on the k-space data 432 and the k-space data 424. The second transformation matrix 438 may receive the k-space data 424 as an input and output the k-space data 432 as an output.

The computing device 100 corrects the first partial k-space subset data using the first transformation matrix

416. For example, by referring to FIG. 4, the k-space data 410 may be replaced by k-space data 411 that is obtained as an output of the first transformation matrix 416 which receives the k-space data 420 as an input. Similarly, the k-space data 414 may be replaced by k-space data 413 that is obtained as an output of the first transformation matrix 416 which receives the k-space data 424 as an input.

The computing device 100 corrects the second partial k-space subset data using the second transformation matrix. For example, by referring to FIG. 4, the k-space data 430 may be replaced by k-space data 431 that is obtained as an output of the second transformation matrix 438 which receives the k-space data 420 as an input. Similarly, the k-space data 434 may be replaced by k-space data 433 that is obtained as an output of the second transformation matrix 438 which receives the k-space data 424 as an input.

Referring back to FIG. 2, in step 250, the computing device 100 combines the registered first partial k-space subset data and the registered second partial k-space subset data to form full k-space dataset. In embodiment, by referring to FIG. 3, the computing device 100 may combine the registered first partial k-space subset data 332 and registered second partial k-space subset data 334 to form full k-space dataset 340. The registered first partial k-space subset data 332 is related to positive echoes and does not include Nyquist ghost. The registered second partial k-space subset data 334 is related to negative echoes and does not include Nyquist ghost.

Figure 8:
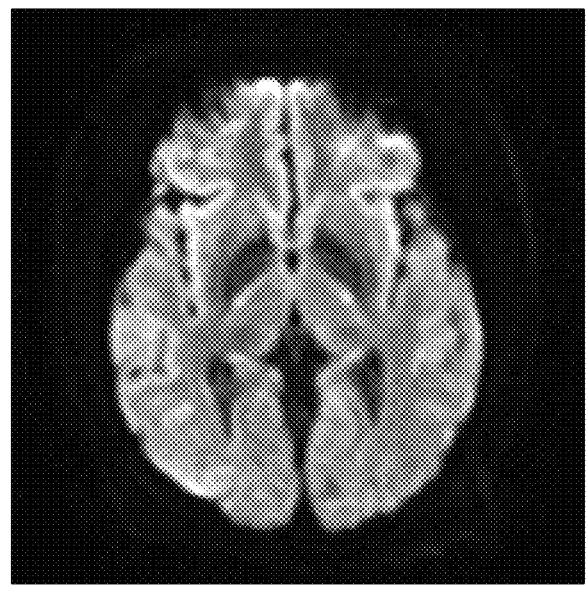
FIG. 8 an exemplary brain image corrected, according to one example in the present disclosure.

Referring back to FIG. 2, in step 260, the computing device 100 reconstructs an image for the object based on the full k-space dataset. By referring to FIG. 3, the computing device 100 reconstructs an image 350 for the object based on the full k-space dataset. In embodiments, the computing device 100 implements inverse-Fourier transform on the full k-space dataset to construct an image for the target area, e.g., the image 350 in FIG. 3. The acquired image may be used for diagnosis, prognosis, surrogate endpoint, or therapeutic response. In some embodiments, the acquired image may be analyzed using computer-aided diagnosis. The computer-aided diagnosis may include a quantification of at least one of volumetric, image intensity, or surface of at least a portion of a region of interest, perfusion, blood volume, flow velocity, relaxation time, diffusion coefficient, proton density, or electro-magnetic properties. FIG. 8 an exemplary brain image which is corrected by the procedure described in FIG. 2. The obtained brain image in FIG. 8 is reconstructed from the full k-space dataset obtained in step 250 of FIG. 2. The resulting image shows the significant reduction of N/2 ghost or Nyquist ghost.

Figure 5:
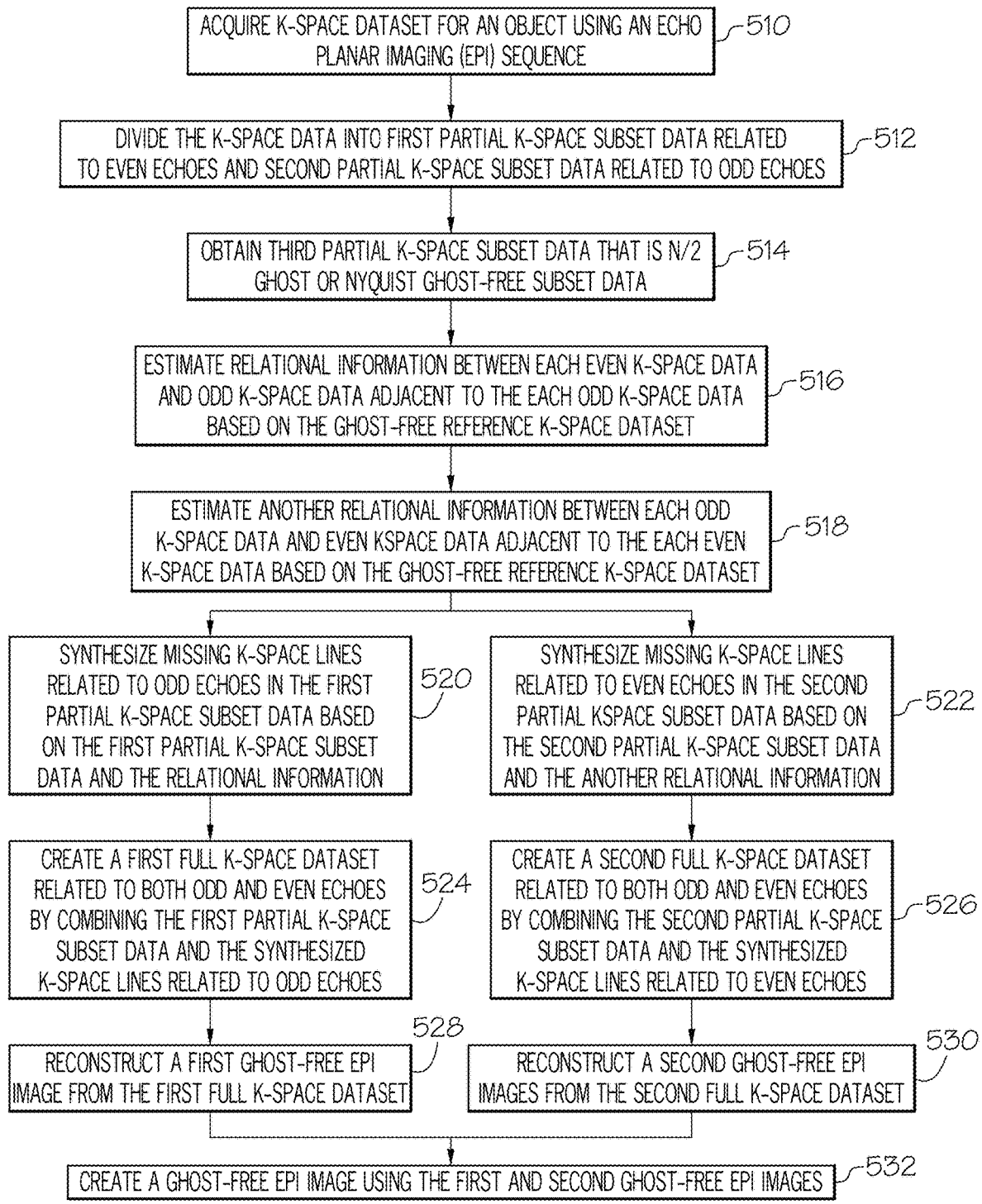
FIG. 5 depicts a flowchart for correcting Nyquist ghost in an EPI image, according to another embodiment shown and described herein.

FIG. 5 depicts a flowchart for correcting Nyquist ghost in an EPI image, according to another embodiment shown and described herein.

In step 510, the computing device 100 acquires k-space dataset for an object using an echo planar imaging (EPI) sequence. In embodiments, as shown in FIG. 1, the computing device 100 receives MR signals from the transmitting and receiving unit 16 and acquires a k-space dataset for the object 9. For example, the k-space dataset 310 in FIG. 3 may be acquired.

In embodiments, the k-space dataset may be acquired in phase-encoding directions. In some embodiments, the k-space dataset is acquired in frequency-encoding directions. In some embodiments, the k-space dataset may be acquired using a combination of partial Fourier acquisition and other under-sampling techniques, such as compressed sensing and parallel imaging acquisitions.

In step 512, the computing device 100 divides the k-space data into first partial k-space subset data related to even echoes and second partial k-space subset data related to odd echoes.

Figure 6:
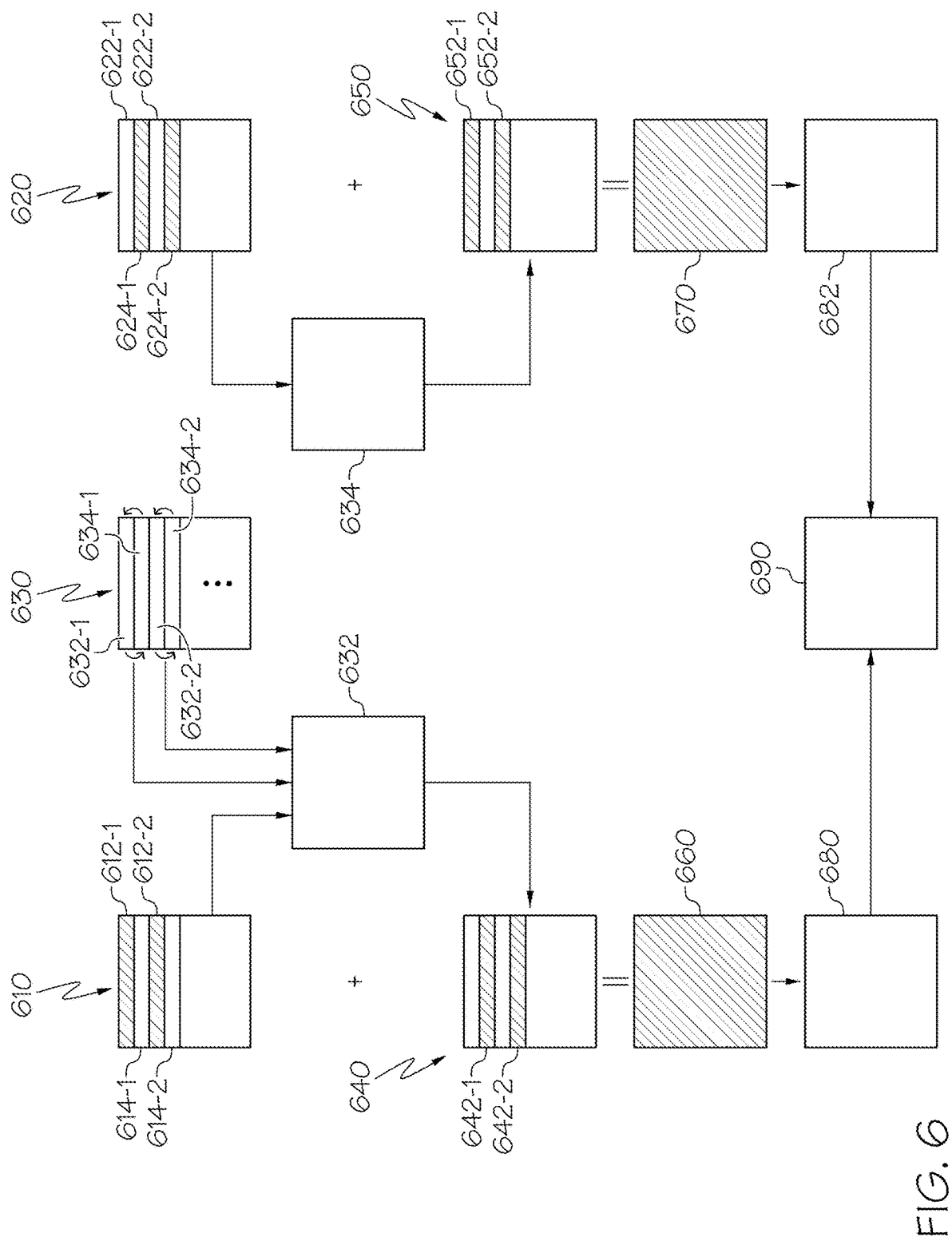
FIG. 6 schematically depicts an example operation for correcting Nyquist ghost in an EPI image, according to one example in the present disclosure.

By referring to FIG. 6, in embodiments, the computing device 100 divides the k-space dataset 310 into first partial k-space subset data 610 related to even echoes and second partial k-space subset data 620 related to odd echoes. The first partial k-space subset data 610 includes k-space lines 612-1, 612-2, and the like related to even echoes. k-space lines 614-1, 614-2, and the like are missing k-space lines. That is, the first partial k-space subset data 610 does not include information about k-space lines 614-1, 614-2, and the like.

The second partial k-space subset data 620 includes k-space lines 624-1, 624-2, and the like related to odd echoes. K-space lines 622-1, 622-2, and the like are missing k-space lines. That is, the second partial k-space subset data 620 does not include information about k-space lines 622-1, 622-2, and the like.

In step 514, the computing device 100 obtains third partial k-space subset data that is N/2 ghost-free or Nyquist ghost-free subset data. In embodiments, the computing device 100 obtains the third partial k-space subset data 630 illustrated in FIG. 6. For example, the third partial k-space subset data 630 may be obtained from the acquired k-space dataset 310. As another example, the third partial k-space subset data 630 may be obtained from additional MR scanning. In embodiments, the k-space dataset 310 is acquired using non-uniform phase encoding, and the third partial k-space subset data 630 is obtained from the k-space dataset 310 acquired using the non-uniform phase encoding.

In embodiment, the Nyquist ghost-free subset data may be acquired with EPI sequence. For example, the Nyquist ghost-free subset data may be conducted interleaved dual echo with acceleration EPI. As another example, the Nyquist ghost-free subset data may be provided by the images which have been acquired by conventional MRI sequences in routine clinical practice and research. For example, $T_1$-weighted and $T_2$-weighted images are often acquired before EPI sequences as a reference for position. As another example, a low spatial resolution image may be acquired by conventional gradient echo and fast spin echo as the Nyquist ghost-free subset data.

In step 516, the computing device 100 estimates relational information between each even k-space data and odd k-space data adjacent to the each even k-space data based on the ghost-free reference k-space dataset. By referring to FIG. 6, the computing device 100 may estimate relational information 632 between each even k-space data and odd k-space data adjacent to the each even k-space data based on the ghost-free reference k-space dataset 630. The relational information may include, but is not limited to, transformation matrix, linear relationship or non-linear relationship between each even k-space data and odd k-space data adjacent to the even odd k-space data of the ghost-free reference k-space dataset 630. For example, the computing device 100 may estimate the relational information 632 between even k-space data 632-1 and the odd k-space data 634-1 adjacent to the even k-space data 632-1. Similarly, the computing device 100 may estimate the relational information between even k-space data 632-2 and the odd k-space data 634-2 adjacent to the even k-space data 632-2.

In step 518, the computing device 100 estimates another relational information between each odd k-space data and even k-space data adjacent to the each odd k-space data based on the ghost-free reference k-space dataset. By referring to FIG. 6, the computing device 100 may estimate relational information 634 between each odd k-space data and even k-space data adjacent to the odd even k-space data based on the ghost-free reference k-space dataset 630. The relational information may include, but is not limited to, transformation matrix, linear relationship or non-linear relationship between each odd k-space data and even k-space data adjacent to the each odd k-space data of the ghost-free reference k-space dataset 630. For example, the computing device 100 may estimate the relational information 634 between odd k-space data 634-1 and even k-space data 632-1 adjacent to the odd k-space data 634-1. Similarly, the computing device 100 may estimate the relation information between odd k-space data 634-2 and the even k-space data 632-2 adjacent to the odd k-space data 634-2.

In step 520, the computing device 100 synthesizes missing k-space lines related to odd echoes in the first partial k-space subset data based on the first partial k-space subset data and the relational information. By referring to FIG. 6, the computing device 100 synthesizes missing k-space lines related to odd echoes 640 based on the first partial k-space subset data 610 and the relational information 632. For example, the computing device 100 synthesizes a k-space line 642-1 related to odd echoes based on the k-space line 612-1 and the relational information 632. Specifically, the relational information 632 may be a transformation matrix that receives the k-space line 612-1 as an input and output the k-space line 642-1 as an output. The synthesized k-space line 642-1 corresponds to the missing k-space line 614-1 of the first partial k-space subset data 610. Similarly, the computing device 100 synthesizes a k-space line 642-2 related to odd echoes based on the k-space line 612-2 and the relational information 632. Specifically, the relational information 632 may be a transformation matrix that receives the k-space line 612-2 as an input and output the k-space line 642-2 as an output. The synthesized k-space line 642-2 corresponds to the missing k-space line 614-2 of the first partial k-space subset data 610.

In step 522, the computing device 100 synthesizes missing k-space lines related to even echoes in the second partial k-space subset data based on the second partial k-space subset data and the another relational information. By referring to FIG. 6, the computing device 100 synthesizes missing k-space lines related to even echoes 650 based on the second partial k-space subset data 620 and the relational information 634. For example, the computing device 100 synthesizes a k-space line 652-1 related to even echoes based on the k-space line 624-1 and the relational information 634. Specifically, the relational information 634 may be a transformation matrix that receives the k-space line 624-1 as an input and output the k-space line 652-1 as an output. The synthesized k-space line 652-1 corresponds to the missing k-space line 622-1 of the second partial k-space subset data 620. Similarly, the computing device 100 synthesizes a k-space line 652-2 related to even echoes based on the k-space line 624-2 and the relational information 634. Specifically, the relational information 634 may be a transformation matrix that receives the k-space line 624-2 as an input and output the k-space line 652-2 as an output. The synthesized k-space line 652-2 corresponds to the missing k-space line 622-2 of the second partial k-space subset data 620.

In step 524, the computing device 100 creates a first full k-space dataset related to both odd and even echoes by combining the first partial k-space subset data and the synthesized k-space lines related to odd echoes. By referring to FIG. 6, the computing device 100 combines the first partial k-space subset data 610 and the synthesized k-space lines 640 to create a first full k-space dataset 660.

In step 526, the computing device 100 creates a second full k-space dataset related to both odd and even echoes by combining the second partial k-space subset data and the synthesized k-space lines related to even echoes. By referring to FIG. 6, the computing device 100 combines the second partial k-space subset data 620 and the synthesized k-space lines 650 to create a second full k-space dataset 670.

In step 528, the computing device 100 reconstructs a first ghost-free EPI image from the first full k-space dataset. By referring to FIG. 6, the computing device 100 reconstructs a first ghost-free EPI image 680 from the first full k-space dataset 660. In embodiments, the computing device 100 implements inverse-Fourier transform on the first full k-space dataset 660 to construct the first ghost-free EPI image 680.

In step 530, the computing device 100 reconstructs a second ghost-free EPI images from the second full k-space dataset. By referring to FIG. 6, the computing device 100 reconstructs a second ghost-free EPI image 682 from the second full k-space dataset 670. In embodiments, the computing device 100 implements inverse-Fourier transform on the second full k-space dataset 670 to construct the second ghost-free EPI image 682.

In step 532, the computing device 100 creates a ghost-free EPI image using the first and second ghost-free EPI images. By referring to FIG. 6, the computing device 100 combines the first ghost-free EPI image 680 and the second ghost-free EPI image 682 to create a ghost-free EPI image 690. For example, the average of the first ghost-free EPI image 680 and the second ghost-free EPI image 682 may be obtained as the ghost-free EPI image 690. The average of the first ghost-free EPI image 680 and the second ghost-free EPI image 682 may enhance signal-to-noise ratio (SNR) and/or a contrast-to-noise ratio (CNR). The acquired image may be used for diagnosis, prognosis, surrogate endpoint, or therapeutic response. In some embodiments, the acquired image may be analyzed using computer-aided diagnosis. The computer-aided diagnosis may include a quantification of at least one of volumetric, image intensity, or surface of at least a portion of a region of interest, perfusion, blood volume, flow velocity, relaxation time, diffusion coefficient, proton density, or electro-magnetic properties.

FIG. 9A is a schematic illustrating an example single-shot echo-planar imaging sequence configuration for reducing N/2 ghost or Nyquist ghost of an image acquired with non-uniform phase encoding according to one example in the present disclosure. The sampling for conventional EPI-based sequence is each echo (either an odd echo or an even echo) per one phase encoding step. The sampling of k-space has uniform phase encoding.

Figure 9B:
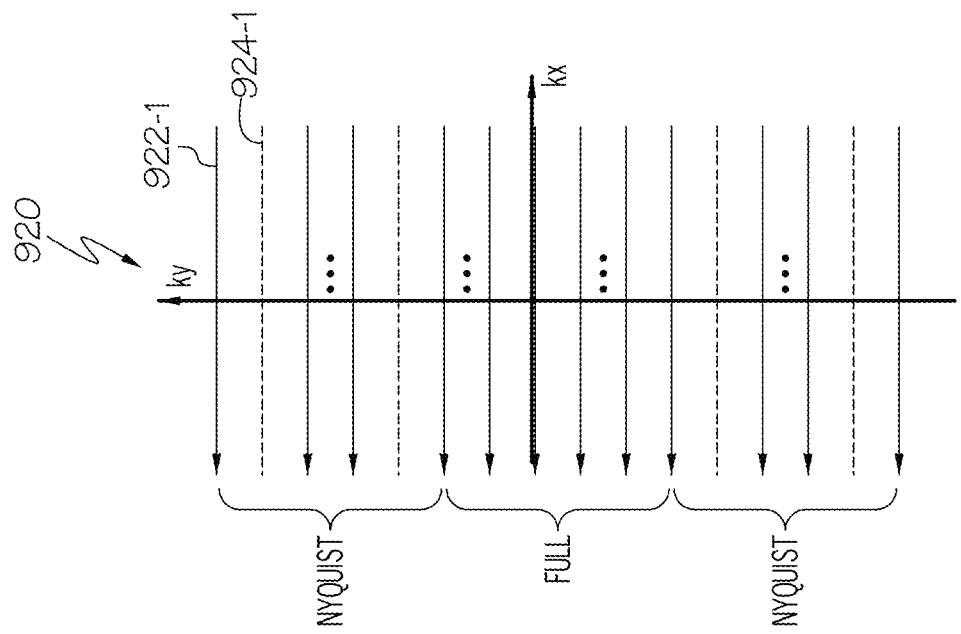
FIG. 9B is a graph illustrating an example of the resulting k-space consists of positive and negative lines from the example single-shot echo-planar imaging sequence with non-uniform phase encoding according to one example in the present disclosure.
Figure 9B:
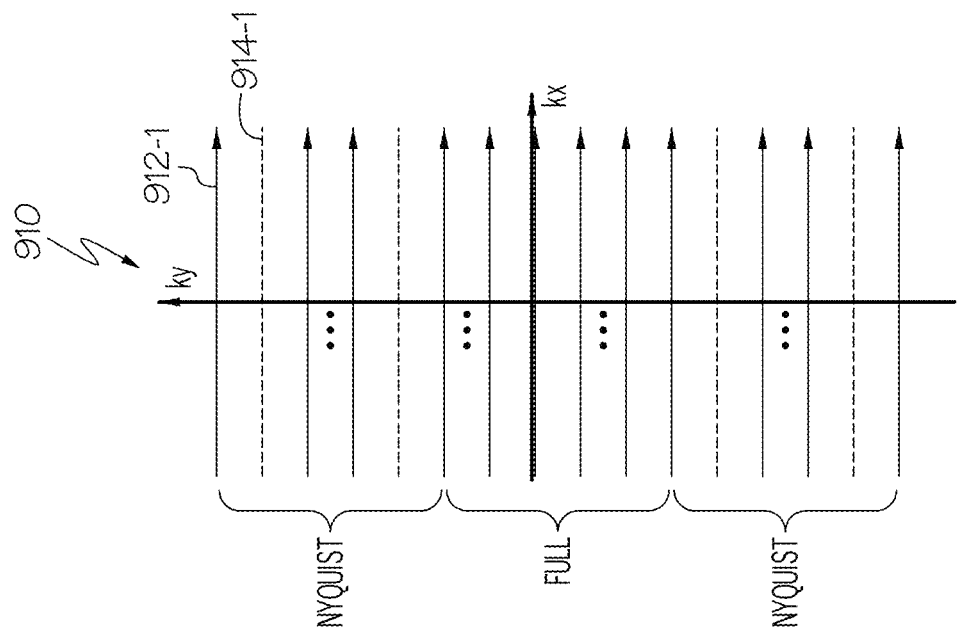

FIG. 9B is a graph illustrating an example of the resulting k-space consists of positive lines 910 and negative lines 920 from the example single-shot echo-planar imaging sequence with non-uniform phase encoding according to one example in the present disclosure. As shown in FIG. 9B, the sampling at the central k-space in the disclosed sequence is two echoes (an odd echo and an even echo) per one phase encoding step, and the sampling at the peripheral k-space data is still one echo per one phase encoding step, so called as non-uniform phase encoding. That is, the low spatial frequency components of k-space sampling is two echoes per each phase-encoding step and the high spatial frequency components of k-space sampling is one echo per each phase-encoding step. The resulting k-space includes central k-space without Nyquist ghost, and the peripheral k-space data with Nyquist ghost. This sequence can be used to acquire an EPI image with reduced artifacts at the cost of a slightly increased scan time.

According to the present disclosure, the corrupted data is corrected by image registration in k-space domain. Since both of even and odd echoes may be corrupted, the systems and methods according to present disclose correct both data related to even and odd echoes. In addition, the systems and methods according to present disclose interleaves the corrected or missing data. Furthermore, according to the present disclosure, the N/2 ghost or Nyquist ghost may be greatly improved by additionally compensated gradient. The disclosed method also improve the geometric distortion caused by susceptibility difference and Bo inhomogeneity in echo planar imaging.

It should be understood that the above-described subject matter may also be implemented as a computer-controlled apparatus, a computer process, a computing system, or an article of manufacture, such as a computer-readable storage medium. It should be understood that the obtained method can be easily extended to correct similar k-space artifacts caused in other sequences that are not echo-planar-imaging based sequences.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

In some embodiments, implementation of the disclosed methods may include generating one or more web pages for facilitating input, output, control, analysis, and other functions. In other embodiments, the methods may be implemented as a locally-controlled program on a local computer system which may or may not be accessible to other computer systems. In still other embodiments, implementation of the methods may include generating and/or operating modules which provide access to portable devices such as laptops, tablet computers, digitizers, digital tablets, smart phones, and other devices.

What is claimed is:

1. A method for reducing N/2 ghost or Nyquist ghost in magnetic resonance (MR) images, the method comprising:
    acquiring k-space dataset for an object using an echo planar imaging (EPI) sequence;
    dividing the k-space dataset into first partial k-space subset data related to positive echoes and second partial k-space subset data related to negative echoes;
    obtaining third partial k-space subset data that is N/2 or Nyquist ghost-free subset data;
    respectively registering the first partial k-space subset data and the second partial k-space subset data to a first portion of the third partial k-space subset data corresponding to positive echoes and a second portion of the third partial k-space subset data corresponding to negative echoes;
    combining the registered first partial k-space subset data and the registered second partial k-space subset data to form full k-space dataset; and
    reconstructing an image for the object based on the full k-space dataset.

2. The method of claim 1, wherein the echo planar imaging sequence is either single-shot EPI sequence or multi-shots EPI sequence.

3. The method of claim 1, wherein the third partial k-space subset data is acquired by the EPI sequence at a time frame different from a time frame when the first partial k-space subset data and the second partial k-space subset data are acquired.

4. The method of claim 1 wherein the third partial k-space subset data is acquired by another EPI sequence different from the EPI sequence, and the third partial k-space subset data and the first and second partial k-space subset data are acquired at a same modality or different modalities.

5. The method of claim 1, wherein acquiring the third partial k-space subset data comprise:
    obtaining the third partial k-space subset data from the acquired k-space dataset; or
    obtaining the third partial k-space subset data from additional MR scanning.

6. The method of claim 5, wherein the k-space dataset is acquired using non-uniform phase-encoding; and
    the third partial k-space subset data is obtained from the k-space dataset acquired using the non-uniform phase encoding.

7. The method of claim 1, wherein registering the first partial k-space subset data and the second partial k-space subset data to the third partial k-space subset data comprises:
    interpolating the third partial k-space subset data into increased resolution k-space dataset which resolution is equal to resolution of the acquired k-space dataset;
    estimating a first transformation matrix based on the first partial k-space subset data and the increased resolution k-space dataset corresponding to the first partial k-space subset data;
    estimating a second transformation matrix based on the second partial k-space subset data and the increased resolution k-space dataset corresponding to the second partial k-space subset data;
    correcting the first partial k-space subset data using the first transformation matrix; and
    correcting the second partial k-space subset data using the second transformation matrix.

8. The method of claim 7, wherein the first transformation matrix reflects variations of translation, rotation or shear data between the first partial k-space subset data and increased resolution k-space subset data, and
    the second transformation matrix reflects variations of translation, rotation or shear data between the second partial k-space subset data and the increased resolution k-space subset data.

9. The method of claim 1, wherein combining the registered first partial k-space subset data and the registered second partial k-space subset data to form the full k-space dataset comprises:
    filling the registered first partial k-space subset data to positive echoes of the full k-space dataset; and
    filling the registered second partial k-space subset data to negative echoes of the full k-space dataset.

10. A method for reducing N/2 ghost or Nyquist ghost in magnetic resonance (MR) images, the method comprising:
    acquiring k-space dataset for an object using an echo planar imaging (EPI) sequence;
    dividing the k-space dataset into first partial k-space subset data related to even echoes and second partial k-space subset data related to odd echoes;
    obtaining third partial k-space subset data that is N/2 or Nyquist ghost-free subset data;

estimating relational information between each even k-space data and odd k-space data adjacent to the each odd k-space data based on the ghost-free reference k-space dataset;

estimating another relational information between each odd k-space data and even k-space data adjacent to the each even k-space data based on the ghost-free reference k-space dataset;

synthesizing missing k-space lines related to odd echoes in the first partial k-space subset data based on the first partial k-space subset data and the relational information;

synthesizing missing k-space lines related to even echoes in the second partial k-space subset data based on the second partial k-space subset data and the another relational information;

creating a first full k-space dataset related to both odd and even echoes by combining the first partial k-space subset data and the synthesized k-space lines related to odd echoes;

creating a second full k-space dataset related to both odd and even echoes by combining the second partial k-space subset data and the synthesized k-space lines related to even echoes;

reconstructing a first ghost-free EPI image from the first full k-space dataset;

reconstructing a second ghost-free EPI images from the second full k-space dataset; and creating a ghost-free EPI image using the first and second ghost-free EPI images.

11. The method of claim 10, wherein obtaining third partial k-space subset data that is N/2 or Nyquist ghost-free subset data further comprises:

obtaining third partial k-space subset data that is N/2 or Nyquist ghost-free subset data corresponding to the first partial k-space subset data; and obtaining third partial k-space subset data that is N/2 or Nyquist ghost-free subset data corresponding to the second partial k-space subset data.

12. The method of claim 10, wherein the relational information includes relational information between each of the missing k-space lines of the first partial k-space subset data and each of k-space lines that are adjacent to the missing k-space lines in the third partial k-space subset data corresponding to the first partial k-space subset data.

13. The method of claim 10, wherein the additional relational information includes relational information between each of the missing k-space lines of the second partial k-space subset data and each of k-space lines that are adjacent to the missing k-space lines in the third partial k-space subset data corresponding to the second partial k-space subset data.

14. A magnetic resonance imaging (MRI) system comprising:

a magnetic field generating unit configured to apply a plurality of RF pulses with a variable flip angle to a target area in the object;

a receiver configured to receive MR signals from the target area;

a processing unit;

a system memory; and machine readable instructions stored in the system memory that, when executed by the processing unit, cause the processing unit to:

acquire k-space dataset for an object using an echo planar imaging (EPI) sequence;

divide the k-space dataset into first partial k-space subset data related to positive echoes and second partial k-space subset data related to negative echoes;

obtain third partial k-space subset data that is N/2 or Nyquist ghost-free subset data;

respectively register the first partial k-space subset data and the second partial k-space subset data to a first portion of the third partial k-space subset data corresponding to positive echoes and a second portion of the third partial k-space subset data corresponding to negative echoes;

combine the registered first partial k-space subset data and the registered second partial k-space subset data to form full k-space dataset; and reconstruct an image for the object based on the full k-space dataset.

15. The system of claim 14, wherein the echo planar imaging sequence is either single-shot EPI sequence or multi-shots EPI sequence.

16. The system of claim 14, wherein the third partial k-space subset data is acquired by the EPI sequence at a time frame different from a time frame when the first partial k-space subset data and the second partial k-space subset data are acquired.

17. The system of claim 14, wherein the third partial k-space subset data is acquired by another EPI sequence different from the EPI sequence, and the third partial k-space subset data and the first and second partial k-space subset data are acquired at a same modality or different modalities.

18. The system of claim 14, wherein the third partial k-space subset data is acquired from the acquired k-space dataset or from additional MR scanning.

19. The system of claim 18, wherein the third partial k-space subset data from the acquired k-space dataset is acquired using the non-uniform phase encoding.

20. The system of claim 14, wherein registering the first partial k-space subset data and the second partial k-space subset data to the third partial k-space subset data comprises:

interpolating the third partial k-space subset data into increased resolution k-space dataset which resolution is equal to resolution of the acquired k-space dataset;

estimating a first transformation matrix based on the first partial k-space subset data and the increased resolution k-space dataset corresponding to the first partial k-space subset data;

estimating a second transformation matrix based on the second partial k-space subset data and the increased resolution k-space dataset corresponding to the second partial k-space subset data;

correcting the first partial k-space subset data using the first transformation matrix; and correcting the second partial k-space subset data using the second transformation matrix.

* * * * *